United States Patent [19]

Fried

[11] Patent Number: 5,495,045
[45] Date of Patent: *Feb. 27, 1996

[54] PROCESS FOR THE PREPARATION OF ALKOXYALKANOIC ACIDS

[75] Inventor: Herbert E. Fried, Houston, Tex.

[73] Assignee: Shell Oil Company, Houston, Tex.

[*] Notice: The portion of the term of this patent shall not extend beyond the expiration date of Pat. No. 5,352,824.

[21] Appl. No.: 363,433

[22] Filed: Dec. 22, 1994

[51] Int. Cl.$^6$ .................... C07C 51/27; C07C 51/235; C07C 51/16
[52] U.S. Cl. .................................. 562/538; 562/540
[58] Field of Search ................................ 562/538, 540

[56] References Cited

U.S. PATENT DOCUMENTS

| | | | |
|---|---|---|---|
| 4,620,033 | 10/1986 | Isshiki et al. | 562/519 |
| 5,136,101 | 8/1992 | Fried | 568/402 |
| 5,136,102 | 8/1992 | Fried | 568/402 |
| 5,136,103 | 8/1992 | Fried | 568/402 |
| 5,155,278 | 10/1992 | Fried | 568/471 |
| 5,155,279 | 10/1992 | Fried | 568/471 |
| 5,155,280 | 10/1992 | Fried | 568/471 |
| 5,162,579 | 11/1992 | Fried | 562/537 |
| 5,166,422 | 11/1992 | Fried | 562/537 |
| 5,166,423 | 11/1992 | Fried | 562/537 |
| 5,175,359 | 12/1992 | Fried | 562/537 |
| 5,175,360 | 12/1992 | Fried | 562/538 |
| 5,179,218 | 1/1993 | Fried | 554/134 |
| 5,352,824 | 10/1994 | Fried | 562/538 |

FOREIGN PATENT DOCUMENTS 5096516 7/1975 Japan.

OTHER PUBLICATIONS

Miyazawa et al., "Oxidation of Benzyl Alcohol with Iron(III) Using Polymers Containing Nitroxyl Radical Structure as a Mediator," J. Polym. Sci., Polym. Chem. Ed., 23 (9), 1985, pp. 2487–2494 (Abstract. Only).

Grigor'ev et al., "Participation of Nitroxyl Radical in the Oxidation of Aldehyde and Alcohol Groups in 3–imidazolin–1–oxyls," Izc. Akad. Nauk SSSR, Ser. Khim., (1), 1978, pp. 208–210. (Abstract Only).

Miyazawa et al., "Oxidation of Benzyl Alcohol with Copper(II) Mediated by a Polymeric Oxoaminium Salt," J. Mol. Catal., 49(1), 1988, 131–134. (Abstract Only).

Ganem et al., "Biological Spin Labels as Organic Reagents. Oxidation of Alcohols to Carbonyl Compounds Using Nitroxyls," J. Org. Chem., 40(13), 1975, pp. 1998–2000.

Annelli et al., "Fast and Selective Oxidation of Primary Alcohols to Aldehydes or to Carboxylic Acids and of Secondary Alcohols to Ketones Mediated by Oxoammonium Salts under Two–Phase Conditions," J. Org. Chem., 52(12), 1987, pp. 2559–2562.

Inokuchi et al., "A Selective and Efficient Method for Alcohol Oxidations Mediated by N–Oxoammonium Salts in Combination with Sodium Bromite," J. Org. Chem., 1990, 55 pp. 462–466.

Organic Synthesis, vol. 69, p. 212 (1990).

Semmelhack et al., "Oxidation of Alcohols to Aldehydes with Oxygen and Cupric Ion, Mediated by Nitrosonium Ion," J. Am. Chem. Soc., 1984, 106, 3374–3376.

Yamaguchi et al., "Application of Redox System Based on Nitroxides to Organic Synthesis," Pure & Applied Chemistry, vol. 62(2), 1990, 217–222.

E. R. Kagan et al., "Chemistry of Hindered Amines from the Piperidine Series", Synthesis, 1984, pp. 895–916.

R. M. Dupeyre et al., "Nitrides. XIX. Norpseudopelletierine–N–oxyl, a New, Stable, Unhindered Free Radical," JACS, 88 (13), 1966, pp. 3180–3181.

E. R. Rozantsev et al., "Synthesis and Reaction of Stable Nitroxyl Radicals I. Synthesis" Synthesis, Apr. 1971, pp. 190–202.

E. R. Rozantsev et al., "Synthesis and Reaction of Stable Nitroxyl Radicals II. Reactions," Synthesis, Apr. 1971, pp. 401–414.

Primary Examiner—José G. Dees
Assistant Examiner—Barbara S. Frazier

[57] ABSTRACT

A process for the preparation of an alkoxyalkanoic acid by reacting the corresponding alkoxyalkanol with a stable free radical nitroxide in the presence of a cerium salt, a highly polar solvent, an oxidant and water, at a temperature in the range of from about 0° C. to about 100° C. and thereafter separating out the alkoxyalkanoic acid.

19 Claims, No Drawings

PROCESS FOR THE PREPARATION OF ALKOXYALKANOIC ACIDS

FIELD OF THE INVENTION

This invention relates to a process for the preparation of alkoxyalkanoic acids by the oxidation of the corresponding alkoxyalkanols in the presence of a stable free radical nitroxide, a cerium salt, a nitrite compound, a highly polar solvent, an oxidant and water.

BACKGROUND OF THE INVENTION

Alkoxyalkanoic acids are useful as anionic detergents and emulsifying agents. These acids, being composed of only the elements C, H and O, do not pose the environmental problems that other detergents containing heteroatoms such as N, S and P pose. Commercially, the alkoxyalkanoic acids are prepared in a two-step process of first reacting an alkoxyalkanol with sodium and then reacting the resultant alkoxide with the sodium salt of chloroacetic acid.

It is also known to convert alkoxyalkanols such as methyl carbitol to the corresponding carboxylic acids by oxidizing them with nitric acid. However, not all of the nitric acid can be separated by distillation, and the reaction product contains nitric acid, which is corrosive and therefore undesirable. In addition, cleavage of the ether linkages occurs to a large degree during this process.

Japanese Patent No. 50-96519 issued on Jul. 31, 1975, discloses a process for the preparation of carboxylic acid salts by the liquid phase dehydrogenation of alcohols with caustic alkali in the presence of precious metal catalysts, including palladium. This process uses a relatively high temperature, 100° C.–270° C. These high temperatures can degrade the ether linkages, especially in the highly ethoxylated alcohols.

It is known to use nitroxyl radicals/oxoammonium salts in the oxidation of primary alcohols to produce aldehydes and acids and secondary alcohols to ketones (*Journal of Organic Chemistry*, Vol. 52 (12), pp. 2559– 2562, and *Journal of Organic Chemistry*, Vol. 55, 1990, pp. 462–466).

It is also reported in the open literature that primary aliphatic alcohols can be converted to aldehydes in 30–40% yields in the presence of catalytic amounts of cuprous chloride, 2,2,6,6,-tetramethylpiperidine-1-oxyl, and atmospheric oxygen (*Journal of American Chemical Society*, 1984, 106, pp. 3374). It is also known that higher yields of aldehydes can be obtained if stoichiometric amounts of cupric or ferric salts are used instead of catalytic amounts of the cuprous salts (*Pure and Applied Chemistry*, vol. 62(2), 1990, pp. 217–222).

It is generally more difficult to oxidize alkoxyalkanols than alkanols as it is difficult to oxidize alkoxyalkanols without splitting the molecular chain at the ether linkage and thereby produce a large proportion of undesired by-product.

It has been found that alkoxyalkanoic acids can be produced in good yields from alkoxyalkanols without producing large amounts of highly corrosive, difficult to separate, by-products. This can be accomplished by using catalytic amounts of a stable free radical nitroxide, a cerium salt which is at least partially soluble, a nitrite compound, a highly polar solvent, and an oxidant.

SUMMARY OF THE INVENTION

This invention relates to a process for the preparation of an alkoxyalkanoic acid of the formula $RO(CH_2CHR'O)_nCH_2CO_2H$ wherein R is an alkyl group of from about 1 to about 22 carbon atoms, R' is hydrogen or alkyl or mixtures thereof (on the individual molecule) and n is an integer of from about 1 to about 500 which comprises reacting the corresponding alkoxyalkanol with a stable free radical nitroxide having the formula:

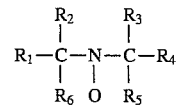

wherein (1) (a) each of $R_1$, $R_2$, $R_3$ and $R_4$ is an alkyl, aryl or substituted alkyl group having 1 to about 15 carbon atoms, and (b) $R_5$ and $R_6$ (i) each is an alkyl group having 1 to about 15 carbon atoms provided that $R_1$–$R_6$, are not all alkyl groups, or a substituted alkyl group having 1 to about 15 carbon atoms wherein the substituent is hydrogen, cyano, —$CONH_2$, —OCOCH, $OCOC_2H_5$, carbonyl, alkenyl wherein the double bond is not conjugated with the nitroxide moiety, or —COOR wherein R of the —COOR group is alkyl or aryl, or (ii) together form part of a ring that contains at least 3 carbon atoms and up to two heteroatoms of O or N, or (2) th

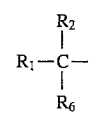

moiety and th

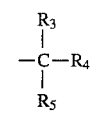

moiety individually are aryl, or (3) th

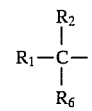

moiety and th

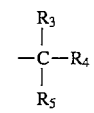

moiety together form a bicyclic ring with the proviso that the group directly adjacent to the N—O moiety is a bridgehead C—H, or a fully alkylated carbon, in the presence of a cerium salt which is at least partially soluble, a nitrite compound, a highly polar solvent, an oxidant and water, at a temperature in the range of from about 0° C. to about 100° C. and thereafter separating out the alkoxyalkanoic acid.

DESCRIPTION OF THE PREFERRED EMBODIMENTS

The present process converts alkoxyalkanols of the formula $RO(CH_2CHR'O)_nCH_2CH_2OH$ (I) wherein R is an alkyl group having from about 1 to about 22 carbon atoms, preferably from about 11 to about 18 carbon atoms, R' is hydrogen or alkyl or mixtures thereof (on the individual molecule) and n represents the average number of oxyalkylene groups and is an integer of from about 1 to about 500, preferably from about 1 to about 50, more preferably 1 to about 12, and most preferably from about 2 to about 9, to the corresponding alkoxyalkanoic acids of the formula $RO(CH_2CHR'O)_nCH_2CO_2H$ (II) by contacting the alkoxyalkanol with a stable free radical nitroxide in the presence of a cerium salt, a nitrite compound, a highly polar solvent, an oxidant and water, at a temperature in the range of from about 0° C. to about 100° C. and thereafter separating out the alkoxyalkanoic acid. The R group in the above formula I can be substituted with any substituent which does not interfere with the oxidation of the hydroxy group. Such substituents include —OR", —$CH_3$, —COOH, $CONH_2$ and COOR" wherein R' is an alkyl or aryl group. The process of the instant invention is particularly suited to detergent range ethoxylated, or propoxylated alcohols with alkyl chains (R) of about 8 to about 20, preferably about 11 to about 18 carbon atoms. The R' groups on an individual molecule can be hydrogen, alkyl, or mixtures thereof. For example, straight ethoxylated, straight propoxylated and mixed ethoxylated-propoxylated detergent alcohols are commercially available. The number of such alkoxylate groups, $CH_2CHR'O$, ranges from about 1 to about 500. Commercially, detergent range ethoxylate alcohols are available with an average of 3, 7, 9 and 12 ethoxylate units per molecule. Others can be readily prepared. In a preferred embodiment, the alkoxyalkanol reactant is an ethoxylated alcohol which has had the unreacted alcohols and lower ethoxylates topped off in order to give an ethoxylate product having less than about 5 percent by weight of the starting alkanol.

The term "stable free radical nitroxide" as used herein shall mean a free radical nitroxide that can be prepared by conventional chemical methods and will exist long enough to be used in a subsequent chemical reaction or examined in a static system by normal methods of spectroscopy. Generally, the stable free radical nitroxides of the present invention have a half life of at least one year. The term "stable free radical" shall also be understood to include the precursor to a stable free radical from which the stable free radical may be produced in situ.

The stable free radical nitroxides, as used in the present process, are precursors to catalysts, i.e., oxoammonium salts, active for the oxidation of alkoxyalkanols to the corresponding acids. These catalysts are generated in situ by the oxidation of a stable free radical nitroxide to an oxoammonium salt. The stable free radical nitroxide can be obtained by the oxidation of amines or hydroxylamines.

The stable free radical nitroxides which are suitable for use in the instant invention have the formula:

wherein each of $R_1$, $R_2$, $R_3$ and $R_4$ is an alkyl, aryl or substituted alkyl groups and no hydrogen is bound to the remaining valences on the carbon atoms bound to the nitrogen. As used herein, the term "alkyl" is meant to include cycloalkyl. The alkyl (or substituted) groups $R_1$–$R_4$ may be the same or different, and preferably contain 1 to 15 carbon atoms. Preferably, $R_1$–$R_4$ are methyl, ethyl, or propyl groups. In addition to hydrogen, the substituents may include, halogen, oxygen, nitrogen and the like.

The remaining valences ($R_5$ and $R_6$) in formula III above may be satisfied by any atom or group except hydrogen which can bond covalently to carbon, although some groups may reduce the stabilizing power of the nitroxide and are undesirable. When $R_1$, $R_2$, $R_3$ and $R_4$ are each alkyl groups, however, at least one of $R_5$ and $R_6$ must be an aryl group. Preferably, $R_5$ and $R_6$ are substituted alkyl groups having 1 to about 15 carbon atoms wherein the substituent is selected from halogen, cyano, —COOR, wherein R is alkyl or aryl, —$CONH_2$, —$OCOC_2H_5$, carbonyl, or alkenyl where the double bond is not conjugated with the nitroxide moiety, or alkyl groups of 1 to about 15 carbon atoms.

The remaining valences ($R_5$ and $R_6$) in formula III above may also form a ring containing at least three carbon atoms and up to two heteroatoms, such as O or N. $R_5$ and $R_6$ can, for example, form a five-membered ring containing 3 carbon atoms and up to two heteroatoms, such as O or N, a five-membered ring containing 4 carbon atoms, a six-membered ring containing 5 carbon atoms, a seven-membered ring containing 6 carbon atoms, an eight-membered ring containing 7 carbon atoms, etc. For purposes of this invention, it is preferred that $R_5$ and $R_6$ together form a five-membered ring, a six-membered ring, a seven-membered ring, or an eight-membered ring, although larger rings would also be suitable. Examples of suitable compounds having the structure above and in which $R_5$ and $R_6$ form part of the ring are 2,2,6,6,-tetramethylpiperidine-1-oxyl ,2,2,5,5-tetramethylpyrrolidin-1-oxyl, 2,2,7,7-tetramethylcycloheptan-1-oxyl, mixtures thereof, and the like. It is understood that these compounds may contain substituents which do not interfere with the reaction.

Th

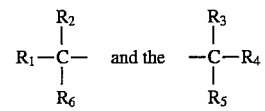

moieties in formula III above can individually be aryl, i.e.

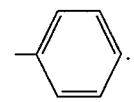

Examples of suitable compounds having the structure above in which th

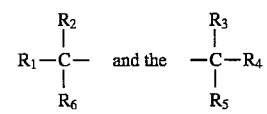

moieties are individually aryl are diphenylamine-N-oxyl, phenyl tertiary butylamine-N-oxyl, 3-methyl-diphenylamine-N-oxyl, 2-chlorophenylamine-N-oxyl and the like. These compounds may be substituted with an substituents which do not interfere with the reaction.

Th

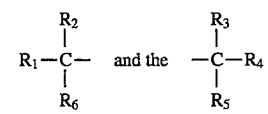

moieties in formula III above can also form a bicyclic ring wherein the group adjacent to the N-O moiety is either a bridgehead C—H or a quaternary carbon. As used herein, the term "bridgehead C—H" refers to a tertiary carbon which is common to both rings of the bicyclic ring system. As used herein, "a quaternary carbon" refers to a fully substituted carbon atom having alkyl, aryl or substituted alkyl groups having 1 to about 18 carbon atoms as substituents. Examples of suitable compounds having the structure above in which the

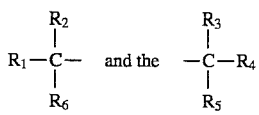

moieties form a bicyclic ring are 2-azabicyclo-[ 2.2.1 ]heptan-2-oxyl, 2-azabicyclo[2.2.2]-3,3-dimethyloctan-2-oxyl, 3-azabicyclo[ 3.2.2]-2,2,4,4-tetramethylnonan-3-oxyl and the like. These compounds may be substituted with any substituents which do not interfere with the reaction.

In a preferred embodiment, the stable free radical nitroxide is a piperidine-1-oxyl having the formula:

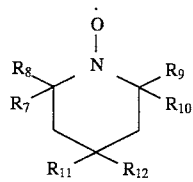

wherein each of $R_7$, $R_8$, $R_9$ and $R_{10}$ is an alkyl, aryl or substituted alkyl group having 1 to about 15 carbon atoms and no hydrogen is bound to the remaining valences on the carbon atoms bound to the nitrogen, and each of $R_{11}$ and $R_{12}$ is alkyl, hydrogen, aryl or a substituted heteroatom. As used herein, the term "alkyl" is meant to include cycloalkyl. The alkyl (or substituted) groups $R_7$–$R_{10}$ may be the same or different, and preferably contain 1 to 15 carbon atoms. Preferably, $R_7$–$R_{10}$ are methyl, ethyl, or propyl groups. In addition to hydrogen, the substituents may include, halogen, oxygen, nitrogen and the like. Typically, one of $R_{11}$ and $R_{12}$ is hydrogen, with the other one being a substituted heteroatom which does not interfere with the reaction. Suitable substituted heteroatoms include —OR

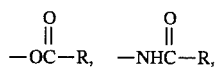

—N$^+$Me$_3$Cl—, —O—SO$_3$H, —O—polymer and the like.

In a particularly preferred embodiment, the nitroxide is selected from the group consisting of 2,2,6,6-tetramethylpiperidine-1-oxyl, 4-hydroxy- 2,2,6,6-tetramethylpiperidine-1-oxyl, 2,2,6,6-tetramethylpiperidine-1-oxyl-4-sulfate, 4-methoxy-2,2,6,6-tetramethylpiperidine-1-oxyl, 4-ethoxy-2,2,6,6 -tetramethylpiperidine-1-oxyl, 4-carbamoyl-2,2,6,6-tetramethylpiperidine-1-oxyl, 4-acetylamino-2,2,6,6-tetramethylpiperidine-1-oxyl, 4-benzoylamino- 2,2,6,6-tetramethylpiperidine-1-oxyl, 4-pivaloylamido-2,2,6,6 -tetramethylpiperidine-1-oxyl, 4-dodecyloylamido-2,2,6,6 -tetramethylpiperidine-1-oxyl, 4-dodecanoylamino-2,2,6,6 -tetramethylpiperidine-1-oxyl, 4-octanoylamino-2,2,6,6 -tetramethylpiperidine-1-oxyl and mixtures thereof, with 2,2,6,6-tetramethylpiperidine-1-oxyl, 4 -acetylamino-2,2,6, 6-tetramethylpiperidine-1-oxyl, and 4-methoxy-2,2,6,6 -tetramethylpiperidine-1-oxyl being especially preferred.

The cerium salt, in conjunction with nitrite in the present process is believed to effect oxidation of the free radical nitroxide to the catalytically active oxoammonium ion. The salt will typically be a halide salt such as a chloride salt, a bromide salt, a nitrate salt, or a fluoride salt, as well as any other cerium salt which is at least partially soluble in the reaction solution. In a preferred embodiment the salt is selected from the group consisting of cerium chloride, cerium bromide, cerium fluoride, cerium nitrate and mixtures thereof. The amount of cerium salt utilized in the present process is typically from about 0.1 mole percent to about 100 mole percent, preferably from about 10 mole percent to about 20 mole percent, basis the starting alkoxyalkanol.

The nitrite compound in the present process is typically selected from the group consisting of sodium nitrite, potassium nitrite and mixtures thereof, with sodium nitrite being preferred. However, any compound which serves to generate nitrite ion during the course of the reaction and which does not interfere with the reaction would be suitable. The amount of nitrite compound utilized in the present process is typically from about 5 mole percent to about 500 mole percent, preferably from about 25 mole percent to about 75 mole percent, basis the starting alkoxyalkanol.

The reaction of the present invention is carried out in the presence of a highly polar solvent. The solvent is generally one in which the alkoxyalkanol is readily soluble. Solvents which are most suitable are highly polar solvents which are inert in the reaction. It is, however, contemplated that the reaction may be carried out in the absence of a solvent or with solvents, other than highly coordinating solvents, such as, for example, ethers, polyethers and alkyl ethoxycarboxylates in the event pressures higher than atmospheric pressure and/or reaction times longer than about 6 hours are utilized. The solvent may be added to the reaction mixture, or alternatively, the nitroxide may be dissolved in the solvent prior to addition of the nitroxide to the reaction medium. The solvent is typically selected from the group consisting of acetonitrile, sulfolane, N-methylpyrrolidinone, acetic acid and mixtures thereof. In a preferred embodiment, the solvent is acetonitrile. The amount of solvent utilized in the process is typically in the range of from about 0.5:1 to about 100:1, preferably from about 2:1 to about 10:1, basis the weight of the starting alkoxyalkanol.

The process of the present invention is also carried out in the presence of an oxidant. The oxidants suitable for use in the instant invention are believed to be those compounds which are capable of oxidizing the metal salts to a form such that they react with the stable free radical nitroxide to form the oxoammonium salt. Suitable oxidants include oxygen-containing gases such as pure oxygen and oxygen in air. Whereas pure oxygen can be preferred to accomplish the desired conversion, the oxygen can also be diluted with an inert gas such as nitrogen, helium, argon, or other similar gas. For purposes of increasing the reaction rate, higher $O_2$ pressures such as, for example, up to about 2000 psig can be utilized. In a preferred embodiment, pure oxygen is used as the oxidant and it is bubbled into the reaction solution at ambient pressure.

The process of the present invention is also carried out in the presence of water. The amount of water typically added is in the range of from about 10 mole percent to about 1000 mole percent, preferably from about 100 mole percent to about 400 mole percent, basis the moles of starting alkoxyalkanol.

The amounts and concentrations of the reactants utilized in the process of the instant invention can vary within wide ranges. The amount of stable free radical nitroxide is typically in the range of from about 0.01 mole percent to about 200 mole percent, preferably from about 5 mole percent to about 20 mole percent, basis the number of moles starting alkoxyalkanol. Generally, the amount of nitrite compound used is in the range of from about 5 mole percent to about 500 mole percent, basis the number of moles of alkoxyalkanol. The amount of cerium salt is typically in the range of from about 0.1 mole percent to about 100 mole percent, preferably from about 10 mole percent to about 20 mole percent, basis the starting alkoxyalkanol.

The process of the present invention is typically conducted under mild conditions, with good results being obtained using a temperature in the range of from about 0° C. to about 100° C., preferably about 20° C. to about 70° C., and most preferably, about 35° C. to about 60° C. Reaction pressures are not critical although higher pressures can result in increased reaction rates. Pressures in the range of from about atmospheric pressure up to about 2000 psig can be employed with good results.

The process of the instant invention can be carried out either batchwise or continuously, using a stirrer equipped reactor or other well known contacting technique to achieve adequate mixing. Preferred reaction conditions, e.g., temperature, pressure, flow rates, etc., vary somewhat depending on the specific nitroxide utilized and on the concentration of the nitroxide.

The process of the instant invention can be carried out in a variety of ways. For example, 0.03 moles of alkoxyalkanol, and 0.006 moles of the nitroxide, 0.001 moles of cerium salt, and solvent may be added to the reaction vessel, followed by the addition of 0.015 moles of sodium nitrite and 0.11 moles of water and bubbling oxygen through the reaction mixture. Following the reaction, the product may be separated from the reaction mixture using conventional procedures such as extraction using a suitable extraction solvent such as, for example, ethyl acetate; evaporation wherein the solvent is stripped from the reaction mixture by using heat or vacuum.

Depending upon process conditions and the nitroxide used, the yields of alkoxyalkanoic acid obtained by this invention are typically at least about 50%. The products produced by the instant process can be used in a variety of detergent applications and emulsifying agents. For example, these products can be used in light duty dishwashing liquids, shampoos, heavy duty laundry liquids and heavy duty powders.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of this invention will be further described by the following embodiments which are provided for illustration and are not to be construed as limiting the invention.

ILLUSTRATIVE EMBODIMENTS

In the following examples, the starting alkoxyalkanol was a NEODOL®Ethoxylate 23-3T alcohol which was prepared by ethoxylating a mixture of $C_{12}$ and $C_{13}$ substantially straight chain alcohols ($C_{12}:C_{13}$~40:60) to form an ethoxylate alcohol having about 3 ethylene oxide units per molecule and then topping off the unreacted alcohols and lower ethoxylates so that the final product has less than about 5 percent by weight of the starting alkanol.

Example 1

12 Grams of NEODOL® Ethoxylate 23-3T, 0.9 grams of 2,2,6,6-tetramethylpiperidine-1-oxyl, 0.5 grams of $CeCl_3$, 1 gram of sodium nitrite, 2 grams of water, and 25 milliliters of acetonitrile were charged to a 100 milliliter round bottomed flask. $O_2$ was bubbled through this mixture at a rate of 35 milliliters/minute at ambient pressure. The reaction temperature was held at 45° C. over a 5-hour period. The results are presented in Table I.

Comparative Example A

Comparative Example A was carried out in a manner similar to Example 1 except that no nitroxide was used. The results are presented in Table I.

Comparative Example B

Comparative Example B was carried out in a manner similar to Example 1 except that no nitrite was used. The results are presented in Table I.

Comparative Example C

Comparative Example C. was carried out in a manner similar to Example 1 except that 1 gram of sodium nitrate was used in the place of 1 gram of sodium nitrite. The results are presented in Table I.

Comparative Example D

Comparative Example D was carried out in a manner similar to Example 1 except that no cerium salt was used. The results are presented in Table I.

As can be seen in Table I, nitroxide, nitrite, and cerium salt are necessary for the oxidation of the alkoxyalkanol to proceed.

TABLE I

| Oxidation of Alkoxyalkanols to Alkoxyalkanoic acids % Yield Alkoxyalkanoic Acids | |
|---|---|
| Example 1 | 53 |
| Comparative Example A | 0 |
| Comparative Example B | 0 |
| Comparative Example C | 0 |
| Comparative Example D | 0 |

What is claimed is:

1. A process for the preparation of an alkoxyalkanoic acid of the formula $RO(CH_2CHR'O)_nCH_2CO_2H$ wherein R is an alkyl group of from about 1 to about 22 carbon atoms, R' is hydrogen or alkyl or mixtures thereof (on the individual molecule) and n is an integer of from about 1 to about 500, which comprises reacting the corresponding alkoxyalkanol with a stable free radical nitroxide having the formula:

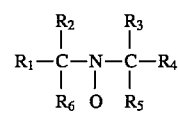

wherein (1) (a) each of $R_1$, $R_2$, $R_3$ and $R_4$ is an alkyl, aryl or heteroatom substituted alkyl group having 1 to about 15 carbon atoms, and (b) $R_5$ and $R_6$ (i) each is an alkyl group having 1 to about 15 carbon atoms provided that $R_1$–$R_6$ are not all alkyl groups, or a substituted alkyl group having 1 to about 15 carbon atoms wherein the substituent is hydrogen, cyano, —$CONH_2$, —$OCOCH$, $OCOC_2H_5$, carbonyl, alkenyl wherein the double bond is not conjugated with the nitroxide moiety, or —COOR wherein R of the —COOR group is alkyl or aryl, or (ii) together form part of a ring that contains at least 3 carbon atoms and up to two heteroatoms of O or N, (2) th

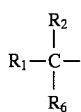

moiety and th

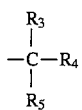

moiety individually are aryl, or (3) th

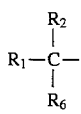

moiety and th

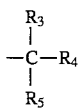

moiety together form a bicyclic ring with the proviso that the group directly adjacent to the N-O moiety is a bridgehead C—H, or a fully alkylated carbon, in the presence of a cerium salt which is at least partially soluble, a nitrite compound, a highly polar solvent, an oxidant and water, at a temperature in the range of from about 0° C. to about 100° C. and thereafter separating out the alkoxyalkanoic acid.

2. The process of claim 1 wherein said alkoxyalkanol has a carbon number in the range from about 11 to about 18.

3. The process of claim 1 wherein the stable free radical nitroxide is selected from the group consisting of 2,2,6,6, -tetramethylpiperidine-1-oxyl, 2,2,5,5-tetramethylpyrrolidin-1-oxyl, 2,2,7,7 -tetramethylcycloheptan-1-oxyl, and mixtures thereof.

4. The process of claim 1 wherein the stable free radical nitroxide has the formula:

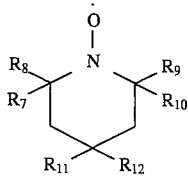

wherein each of $R_7$, $R_8$, $R_9$ and $R_{10}$ is an alkyl, aryl or heteroatom substituted alkyl group having 1 to about 15 carbon atoms and each of $R_{11}$ and $R_{12}$ is alkyl, hydrogen, aryl or a substituted heteroatom.

5. The process of claim 4 wherein the stable free radical nitroxide is selected from the group consisting of 2,2,6,6 -tetramethylpiperidine-1-oxyl, 4-methoxy-2,2,6,6 -tetramethylpiperidine-1-oxyl, 4 -ethoxy-2,2,6,6-tetramethylpiperidine-1-oxyl, 4-acetylamino-2,2,6,6 -tetramethylpiperidine-1-oxyl, 4-carbamoyl-2,2,6,6-tetramethylpiperidine-1-oxyl, 4 -benzoylamino-2,2,6,6-tetra-methylpiperidine-1-oxyl, 4-pivaloylamido-2,2,6,6 -tetramethylpiperidine-1-oxyl, 4-dodecyloylamido-2,2,6,6 -tetramethylpiperidine-1-oxyl, 4-dodecanoylamino-2,2,6,6 -tetramethylpiperidine-1-oxyl, 4-octanoylamino-2,2,6,6 -tetramethylpiperidine-1-oxyl and mixtures thereof.

6. The process of claim 5 wherein the stable free radical nitroxide is selected from the group consisting of 2,2,6,6 -tetramethylpiperidine-1-oxyl, 4-acetylamino-2,2,6,6-tetramethylpiperidine-1-oxyl, 4 -methoxy-2,2,6,6-tetramethylpiperidine-1-oxyl and mixtures thereof.

7. The process of claim 1 wherein said cerium salt is selected from the group consisting of cerium chloride, cerium bromide, cerium nitrate, cerium flouride and mixtures thereof.

8. The process of claim 1 wherein the solvent is selected from the group of acetonitrile, sulfolane, N-methylpyrrolidinone, acetic acid and mixtures thereof.

9. The process of claim 8 wherein the solvent is acetonitrile.

10. The process of claim 1 wherein said nitrite compound is selected from the group consisting of sodium nitrite, potassium nitrite and mixtures thereof.

11. The process of claim 10 wherein said nitrite compound is sodium nitrite.

12. The process of claim 1 wherein the amount of nitrite compound is in the range of from about 5 mole percent to about 500 mole percent, basis the moles of starting alkoxyalkanol.

13. The process of claim 1 wherein said alkoxyalkanol is contacted with said stable free radical nitroxide and said solvent, followed by the addition thereto of said nitrite compound and said cerium salt.

14. The process of claim 13 wherein the amount of stable free radical nitroxide is in the range of from about 0.01 mole percent to about 200 mole percent, basis the number of moles of alkoxyalkanol.

15. The process of claim 13 wherein the amount of nitrite compound is in the range of from about 5 mole percent to about 500 mole percent, basis the number of moles of alkoxyalkanol.

16. The process of claim 1 wherein said oxidant is an oxygen-containing gas.

17. The process of claim 16 wherein said oxygen-containing gas is selected from the group consisting of pure oxygen and air.

18. The process of claim 1 wherein the amount of water is in the range of from about 10 mole percent to about 1000 mole percent, basis the moles of starting alkoxyalkanol.

19. The process of claim 1 wherein said process is carried out at a temperature in the range of from about 20° C. to about 70° C. and at atmospheric pressure.

* * * * *